United States Patent
Roux et al.

(10) Patent No.: US 12,042,596 B2
(45) Date of Patent: Jul. 23, 2024

(54) MOBILE NEGATIVE PRESSURE WOUND THERAPY DEVICE CONFIGURED FOR START-UP TEST

(71) Applicant: Mölnlycke Health Care AB, Gothenburg (SE)

(72) Inventors: Alain Roux, Träslövsläge (SE); Anders Hermansson, Mölnlycke (SE); Stefan Kidborg, Ytterby (SE)

(73) Assignee: Mölnlycke Health Care AB, Gothenburg (SE)

( * ) Notice: Subject to any disclaimer, the term of this patent is extended or adjusted under 35 U.S.C. 154(b) by 0 days.

(21) Appl. No.: 17/998,832

(22) PCT Filed: May 24, 2021

(86) PCT No.: PCT/EP2021/063752
§ 371 (c)(1),
(2) Date: Nov. 15, 2022

(87) PCT Pub. No.: WO2021/239657
PCT Pub. Date: Dec. 2, 2021

(65) Prior Publication Data
US 2023/0201442 A1    Jun. 29, 2023

(30) Foreign Application Priority Data
May 25, 2020  (EP) ..................... 20176285

(51) Int. Cl.
*A61M 1/00* (2006.01)
(52) U.S. Cl.
CPC ............... *A61M 1/73* (2021.05); *A61M 1/90* (2021.05); *A61M 2205/3331* (2013.01)
(58) Field of Classification Search
CPC .......... A61M 1/73; A61M 1/90; A61M 1/984; A61M 1/964; A61M 1/96;
(Continued)

(56) References Cited

U.S. PATENT DOCUMENTS

| 2011/0092958 A1* | 4/2011 | Jacobs ................... A61M 1/96 604/543 |
| 2018/0318476 A1* | 11/2018 | Askem ................... A61M 1/96 |
| 2019/0328982 A1 | 10/2019 | Sarangapani et al. |

FOREIGN PATENT DOCUMENTS

WO    WO 2016/103033 A2    6/2016

OTHER PUBLICATIONS

International Search Report and Written Opinion were mailed on Jul. 6, 2021 by the International Searching Authority for International Application No. PCT/EP2021/063752 filed on May 24, 2021 and published as WO 2021/239657 (Applicant- Molnlycke Health Care AB) (13 pages).

* cited by examiner

*Primary Examiner* — Philip R Wiest
*Assistant Examiner* — Matthew Wrubleski
(74) *Attorney, Agent, or Firm* — Ballard Spahr LLP

(57) ABSTRACT

A mobile negative pressure wound therapy (NPWT) device is described having an inlet to be in fluid flow connection with a wound site; a canister in fluid flow connection with the inlet for collection of liquid from the wound site; a pump in fluid flow connection with the canister for establishing a negative pressure in the canister; a pressure sensor arranged to sense a pressure in the canister; and control circuitry for controlling operation of the NPWT device. The control circuitry is configured to: initiate a test sequence for the NPWT device; acquire a first signal indicating the pressure in the canister; evaluate the first signal; when the acquired first signal indicates a pressure less negative than a predefined threshold pressure: control the pump to operate during a predefined time period; acquire a second signal after the predefined time period; proceed with the start-up test sequence; and when the acquired signal indicates a pressure more negative than the predefined threshold pres- (Continued)

sure: proceed with the start-up test sequence without controlling the pump to operate during the predefined time period.

13 Claims, 4 Drawing Sheets

(58) Field of Classification Search
CPC ...... A61M 2205/3331; A61M 2205/50; A61M 2205/70; A61M 2205/8206; A61M 2205/581; A61M 2209/088
See application file for complete search history.

MOBILE NEGATIVE PRESSURE WOUND THERAPY DEVICE CONFIGURED FOR START-UP TEST

CROSS-REFERENCE TO RELATED APPLICATIONS

This application is a U.S. National Phase Application of International Application No. PCT/EP2021/063752, filed May 24, 2021, which claims priority to European Patent Application No. 20176285.3, filed May 25, 2020, each of which is hereby incorporated by reference in its respective entirety.

FIELD OF THE INVENTION

The present invention relates to a mobile negative pressure wound therapy (NPWT) device, and to a method of testing such an NPWT device.

BACKGROUND OF THE INVENTION

Negative pressure wound therapy (NPWT) is a technique that promotes healing of e.g. surgical, acute and chronic wounds by the application of a negative (that is, sub-atmospheric) pressure to the wound, using a negative pressure pump. The NPWT technique also permits less outside disturbance of the wound as well as provides for transportation of excess fluids away from the wound site. Generally, the NPWT technique has until now mainly been applied to a patient while in a hospital environment. However, recent product development allows the technique to be used by a patient in a home environment.

In order to make it easier and more comfortable for a user to benefit from NPWT, mobile NPWT devices have recently been developed. For such an NPWT device to be truly mobile, it is practically necessary to power the NPWT device with one or several batteries. Naturally, operation of the NPWT device will eventually reduce the amount of energy stored in the battery (or batteries) to such a degree that it becomes necessary to replace the battery with a fully charged battery. Following a battery change, and also at other times, it may be desirable to put the NPWT device through a start-up test sequence to reduce the risk of injury or discomfort for the user.

SUMMARY

It is an object of the present invention to provide an improved NPWT device, and method of testing an NPWT device, in particular providing for an improved start-up test of the NPWT device.

According to a first aspect of the present invention, it is therefore provided a mobile negative pressure wound therapy (NPWT) device, comprising an inlet to be in fluid flow connection with a wound site; a canister in fluid flow connection with the inlet for collection of liquid from the wound site; a pump in fluid flow connection with the canister for establishing a negative pressure in the canister; a pressure sensor arranged to sense a pressure in the canister; and control circuitry for controlling operation of the NPWT device. The control circuitry is configured to receive a request for start-up of the NPWT device; initiate, in response to the request for start-up, a start-up test sequence for the NPWT device; acquire, from the pressure sensor, a first signal indicating the pressure in the canister; evaluate the first signal acquired from the pressure sensor; when the acquired first signal indicates a pressure less negative than a predefined threshold pressure: control the pump to operate during a predefined time period; acquire a second signal from the pressure sensor after the predefined time period; proceed with the start-up test sequence; and allow, unless the NPWT device failed at least one test in the start-up test sequence by failing to fulfill at least one criterion in a set of predefined criteria, the NPWT device to transition to therapy mode; and when the acquired signal indicates a pressure more negative than the predefined threshold pressure: proceed with the start-up test sequence without controlling the pump to operate during the predefined time period; and allow, unless the NPWT device failed at least one test in the start-up test sequence by failing to fulfill at least one criterion in a set of predefined criteria, the NPWT device to transition to therapy mode.

It should be noted that the start-up test sequence may also include a decision to abort the start-up test sequence in the event of a failed test. Accordingly, the step of proceeding with the start-up test sequence may involve aborting the start-up test sequence.

It should also be noted that the pressure sensor need not be arranged to directly sense the pressure in the canister, but that the pressure sensor may be arranged to sense the pressure at another location in the NPWT device, where the sensed pressure is indicative of the pressure in the canister. Furthermore, the pressure sensor may sense another property, such as force or deflection, based on which a change in pressure can be deduced.

The request for start-up may be any indication that it is desired to make the NPWT device ready for therapy. For instance, the request for start-up may be power up (insertion of a battery or batteries), or depression of a start button, or a reset operation, etc.

Where "more negative pressure than a predefined threshold pressure" is referred to, it should be understood that "negative" is in relation to atmospheric pressure, and that this situation is equivalent to the absolute pressure being lower than a predefined absolute threshold pressure.

The present invention is based on the realization that there are possible use cases where there may be negative pressure in the NPWT system before the pump is operated during the start-up test, and that it would be desirable to prevent the pump from operating under such circumstances. It cannot be safely assumed that care staff or the user always follows all instructions for operation of the NPWT system. For example, a plausible and undesirable use case may be that tubing that is flow connected to the outlet of a chamber at the wound site is blocked before battery change or a switch to a new NPWT device, and unblocked following connection to the inlet of the NPWT device after having performed the start-up test. In such a case, there will be negative pressure in the canister of the NPWT device before the start-up test sequence is initiated. For such and other similar cases, the present inventor has found that it would be desirable to avoid performing a regular test of the pressure sensor and pump during the start-up test sequence, but to instead proceed with the start-up test sequence based on a finding that the pressure is more negative than a predefined threshold pressure. The predefined threshold pressure may, for example, be atmospheric pressure, or in other words zero negative pressure. Alternatively, the predefined threshold pressure may be a predefined non-zero negative pressure.

Hereby, the risk of the start-up test resulting in discomfort or even harm to the user after completion of the start-up test and unblocking of the tubing can be reduced.

Furthermore, at least for most use cases, the acquisition of a signal from the pressure sensor indicating a pressure more negative than the predefined threshold pressure is an indication that the pressure sensor works and that the pump has been operational recently, and it can be concluded that there is less risk involved in allowing the NPWT device to transition to therapy mode than in operating the pump during the predefined time period.

The predefined time period may be at least 0.5 s, and may advantageously be closer to 1 s, such as around 0.9 s.

Advantageously, the first signal may be acquired from the pressure sensor before any operation of the pump included in the start-up test sequence.

According to various embodiments, the control circuitry may further be configured to, when the acquired first signal indicates a pressure less negative than the predefined threshold pressure, evaluate the second signal acquired from the pressure sensor; and determine, when the second signal indicates a negative pressure within a predefined interval, that the NPWT device has fulfilled a criterion in the set of predefined criteria. For instance, the control circuitry may be configured to determine that the NPWT device has fulfilled this criterion when the second signal acquired from the pressure sensor indicates a more negative pressure (lower absolute pressure) than what is indicated by the first signal acquired from the pressure sensor.

According to embodiments, the control circuitry may further be configured to, when the acquired first signal indicates a pressure more negative than the predefined threshold pressure, determine that the NPWT has fulfilled a criterion in the set of predefined criteria, without controlling the pump to operate during the predefined time period.

In embodiments, the control circuitry may further be configured to, after the NPWT device has been allowed to transition to therapy mode: repeatedly acquire signals from the pressure sensor while controlling the pump to operate; evaluate the signals acquired from the pressure sensor; and determine that the pressure sensor is non-functional when: the signals acquired from the pressure sensor are constantly at a minimum value that can be acquired from the pressure sensor, or the signals acquired from the pressure sensor are constantly at a maximum value that can be acquired from the pressure sensor, or the signals acquired from the pressure sensor alternate between the minimum value and the maximum value; or the signals acquired from the pressure sensor indicate a pressure that increases over time.

These embodiments cover two important failure modes that are likely to indicate a non-functional pressure sensor. In the first failure mode, the connection between the pump and control circuitry comprised in the NPWT device may be interrupted, and in the second failure mode there may be a problem in amplification circuitry involved in pressure sensing. In the case of an interrupted connection, it has been found that the interrupted electrical conductors connected to the control circuitry may function as an antenna and that a signal acquired by the control circuitry will either be a minimum signal, such as 0 V, or a maximum signal, such as 3.3 V (or any other relevant maximum voltage in the NPWT device). As for problems in the amplification circuitry, it has been found that this may result in an inverted pressure signal curve, indicating an increasing absolute pressure, where there is in fact a decreasing absolute pressure (or more negative pressure in relation to atmospheric pressure).

According to various embodiments, furthermore, the mobile NPWT device may additionally comprise a battery and a speaker, and the control circuitry may be further configured to: control the speaker to operate to emit a sound; measure a drop in battery voltage during operation of the speaker; and determine, when the drop in battery voltage during operation of the speaker is less than a predetermined value, that the NPWT device has fulfilled a criterion in the set of predefined criteria.

According to a second aspect of the present invention, it is provided a method of testing a mobile negative pressure wound therapy (NPWT) device having an inlet to be in fluid flow connection with a wound site, a canister in fluid flow connection with the inlet for collection of liquid from the wound site, a pump in fluid flow connection with the canister for establishing a negative pressure in the canister, and a pressure sensor arranged to sense a pressure in the canister, the method comprising the steps of: receiving a request for start-up of the NPWT device; initiating, in response to the request for start-up, a start-up test including a start-up test sequence for the NPWT device; acquiring, from the pressure sensor, a first signal indicating the pressure in the canister; evaluating the first signal acquired from the pressure sensor; when the acquired first signal indicates a pressure less negative than a predefined threshold pressure: controlling the pump to operate during a predefined time period; acquiring a second signal from the pressure sensor after the predefined time period; proceeding with the start-up test sequence; and determining, unless the NPWT device failed at least one test in the start-up test sequence by failing to fulfill at least one criterion in a set of predefined criteria, that the NPWT device passed the start-up test; and when the acquired signal indicates a pressure more negative than the predefined threshold pressure: proceeding with the start-up test sequence without controlling the pump to operate during the predefined time period; and determining, unless the NPWT device failed at least one test in the start-up test sequence by failing to fulfill at least one criterion in a set of predefined criteria, that the NPWT device passed the start-up test.

Variants and advantages of this second aspect of the invention are largely analogous to those described above in connection with the first aspect.

According to a third aspect of the invention it is provided a computer program comprising instructions for causing the control unit comprised in the NPWT device according to embodiments of the first aspect to carry out the steps of the method according to embodiments of the second aspect, when the computer program is run on the control unit.

The computer program may be stored on a non-transitory computer readable data carrier.

The mobile NPWT device according to embodiments of the present invention may be included in a negative pressure wound therapy (NPWT) system, further comprising a chamber for establishment of a negative pressure, to be arranged at a wound site, the chamber having an outlet, and tubing flow connecting the outlet of the chamber and the inlet of the NPWT device.

In summary, the present invention thus relates to a mobile negative pressure wound therapy (NPWT) device, comprising an inlet to be in fluid flow connection with a wound site; a canister in fluid flow connection with the inlet for collection of liquid from the wound site; a pump in fluid flow connection with the canister for establishing a negative pressure in the canister; a pressure sensor arranged to sense a pressure in the canister; and control circuitry for controlling operation of the NPWT device. The control circuitry is configured to: initiate a test sequence for the NPWT device; acquire a first signal indicating the pressure in the canister; evaluate the first signal; when the acquired first signal indicates a pressure less negative than a predefined threshold pressure: control the pump to operate during a predefined time period; acquire a second signal after the predefined time period; proceed with the start-up test sequence; and when the acquired signal indicates a pressure more negative than the predefined threshold pressure: proceed with the start-up test sequence without controlling the pump to operate during the predefined time period.

BRIEF DESCRIPTION OF THE DRAWINGS

These and other aspects of the present invention will now be described in more detail, with reference to the appended drawings showing example embodiments of the invention, wherein.

DETAILED DESCRIPTION OF EXAMPLE EMBODIMENTS

Figure 1:
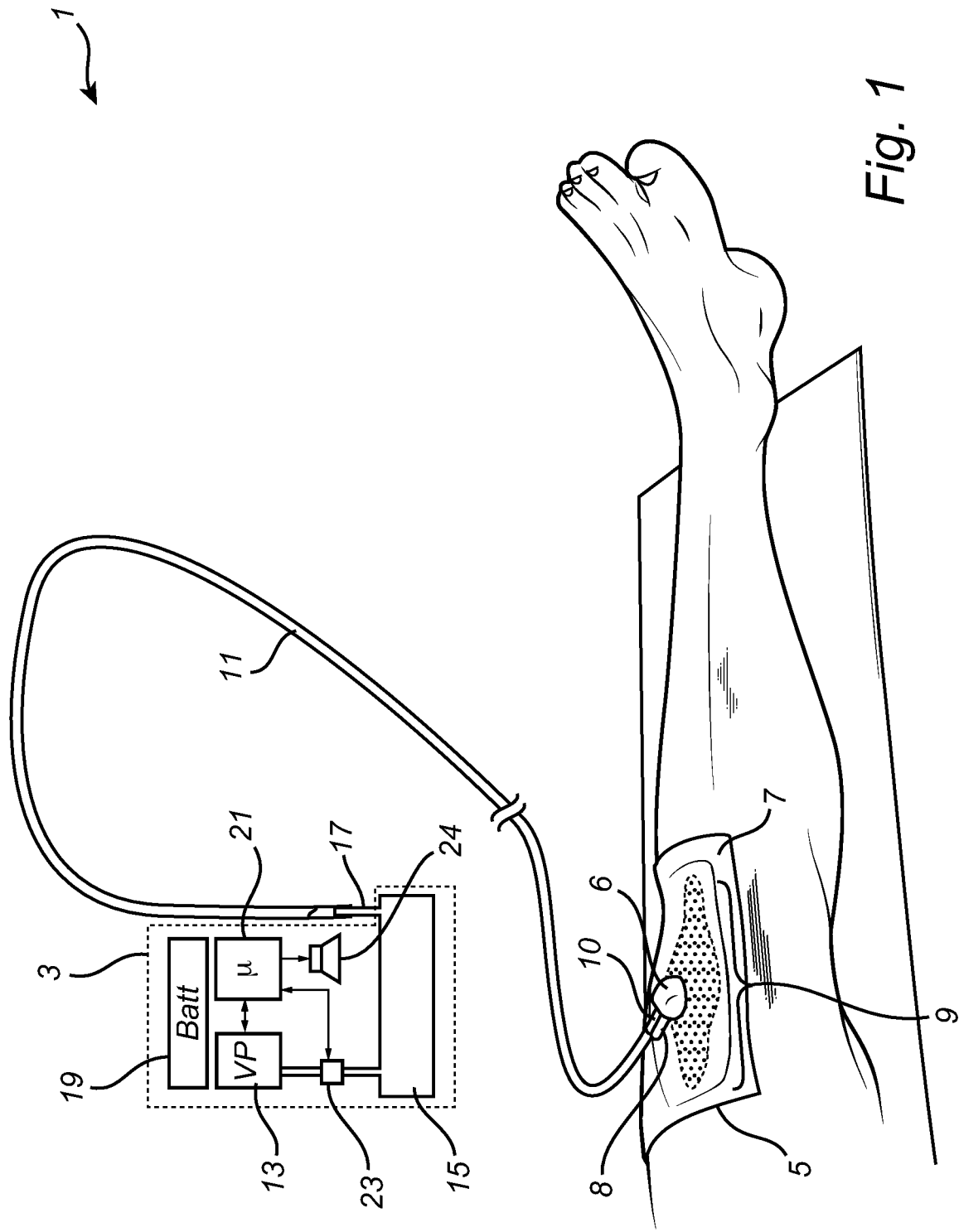
FIG. 1 is an illustration of an exemplary mobile NPWT system according to an embodiment of the present invention.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, there is conceptually illustrated a negative pressure wound therapy (NPWT) system 1, comprising a mobile NPWT device 3 in accordance with an example embodiment of the present invention. The NPWT system 1 further comprises a wound cover 5 with a chamber 6 arranged at a wound site. The wound cover 5, including the chamber 6, is adapted to create a sealed space 7 defined in part by a wound surface 9, such as at the skin of a user, at or around a wound of the user. As is schematically shown in FIG. 1, the chamber 6 has an inlet 8 and an outlet 10. The outlet 10 of the chamber 6 is flow connected to the mobile NPWT device 3 using tubing 11, and the inlet 8 of the chamber 6 is in flow connection with an ambient (the air around the user) through a filter (not visible in FIG. 1) to provide for continuous leakage of air into the chamber 6. The tubing 11 may be any suitable flexible tubing fabricated from elastomeric and/or polymeric materials.

As is schematically shown in FIG. 1, the NPWT device 3 comprises a negative pressure pump 13 adapted for establishing a negative pressure when the negative pressure pump 13 is controlled to operate. The negative pressure pump 13 may be any type of pump that is biocompatible and maintains or draws adequate and therapeutic vacuum levels. Preferably, the negative pressure level to be achieved may be in a range between about −20 mmHg and about −300 mmHg. In a possible embodiment of the present disclosure, a negative pressure range between about −80 mmHg and about −140 mmHg may be used. In a possible embodiment of the present invention, the negative pressure pump 13 is a pump of the diaphragmatic or peristaltic type.

The negative pressure pump 13 is fluid flow connected to a canister 15, the canister 15 also forming part of the NPWT device 3. The canister 15 may be formed from e.g. molded plastic or the like, and may possibly be a detachable component of the NPWT device 3. The canister 15 may preferably be at least partly transparent/translucent to permit viewing the interior of the canister 15 to assist the user in determining the remaining capacity of the canister 15.

An inlet port 17 is formed at the canister 15, for allowing connection to the tubing 11. The inlet port 17 may also be formed elsewhere at the NPWT device 3, however still fluidly connected to the canister 15. The connection between the inlet port 17 and the tubing 11 is a sealed connection, thus ensuring that no leakage is formed at the inlet port 17 during normal operation of the NPWT device 3. The tubing 11 is preferably releasably connected to the inlet port 17 through conventional means including a friction fit, bayonet coupling, snap fit, barbed connector, or the like. The inlet port 17 may be molded/formed from the same material and/or at the same time as forming the canister 15. A similar sealed connection (e.g. using a flange insulation/"O-ring") may be formed between the canister 15 and the negative pressure pump 13.

The NPWT device 3 further comprises a battery 19 for powering the NPWT device 3. The battery 19 may preferably be of the rechargeable type but may alternatively be disposable. A specifically adapted battery pack may be used in relation to some embodiments of the present disclosure.

The NPWT device 3 also comprises a control unit 21 for controlling operation of the mobile NPWT device 3, at least one pressure sensor 23 arranged to sense a pressure in the canister 15, and a speaker 24 for providing user feedback and/or alerts.

The control unit 21, which is powered by the battery 19 and coupled to the pump 13, the pressure sensor 23, and the speaker 24, may include a microprocessor, microcontroller, programmable digital signal processor or another programmable device. The control unit 21 may also, or instead, include an application specific integrated circuit, a programmable gate array or programmable array logic, a programmable logic device, or a digital signal processor. Where the control unit 21 includes a programmable device such as the microprocessor, microcontroller or programmable digital signal processor mentioned above, the processor may further include computer executable code that controls operation of the programmable device.

During use of the NPWT device 3, the wound cover 5 is arranged at a wound site of the user, forming the sealed space 7. The tubing 11 is provided to fluidly connect the outlet 10 of the chamber 6 in the wound cover 5 to the inlet port 17 of the NPWT device 3. To start the therapy, the mobile NPWT device 3 may then be activated, e.g. by the user, by pressing a start/pause button (not shown in FIG. 1). In response to this request to start the therapeutic treatment, the control unit 21 may control the negative pressure pump 13 to operate. When in operation, the negative pressure pump 13 will start to evacuate air through the canister 15, the inlet port 17, the tubing 11 and the sealed space 7 formed by the chamber 6 in the wound cover 5. Accordingly, negative pressure will be created within the sealed space 7. In case a liquid has been formed at the wound site, this liquid from the wound site may at least partly be "drawn" from the wound site, through the tubing 11, the inlet port 17 and into the canister 15 due to the continuous limited leakage provided by the inlet 8 of the chamber 6. The amount of liquid (sometimes referred to as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) may be arranged between the canister 15 and the negative pressure pump 13 to ensure that no liquid is allowed to pass to the negative pressure pump 13 from the canister 15.

As was mentioned above, the mobile NPWT device 3 requires a charged battery pack 19 for operation, and when the battery pack 19 is depleted, it needs to be replaced. Following battery replacement, or if the NPWT device 3 is replaced by a new one, the NPWT device 3 is tested to reduce the risk of malfunction during subsequent therapy.

To that end, the control unit 21 in the NPWT device 3 according to embodiments of the present invention may be configured to carry out test procedures according to embodiments of the present invention. In particular, processing circuitry comprised in the control unit 21 may be programmed to carry out the steps according to various embodiments of the method of the present invention.

Figure 3:
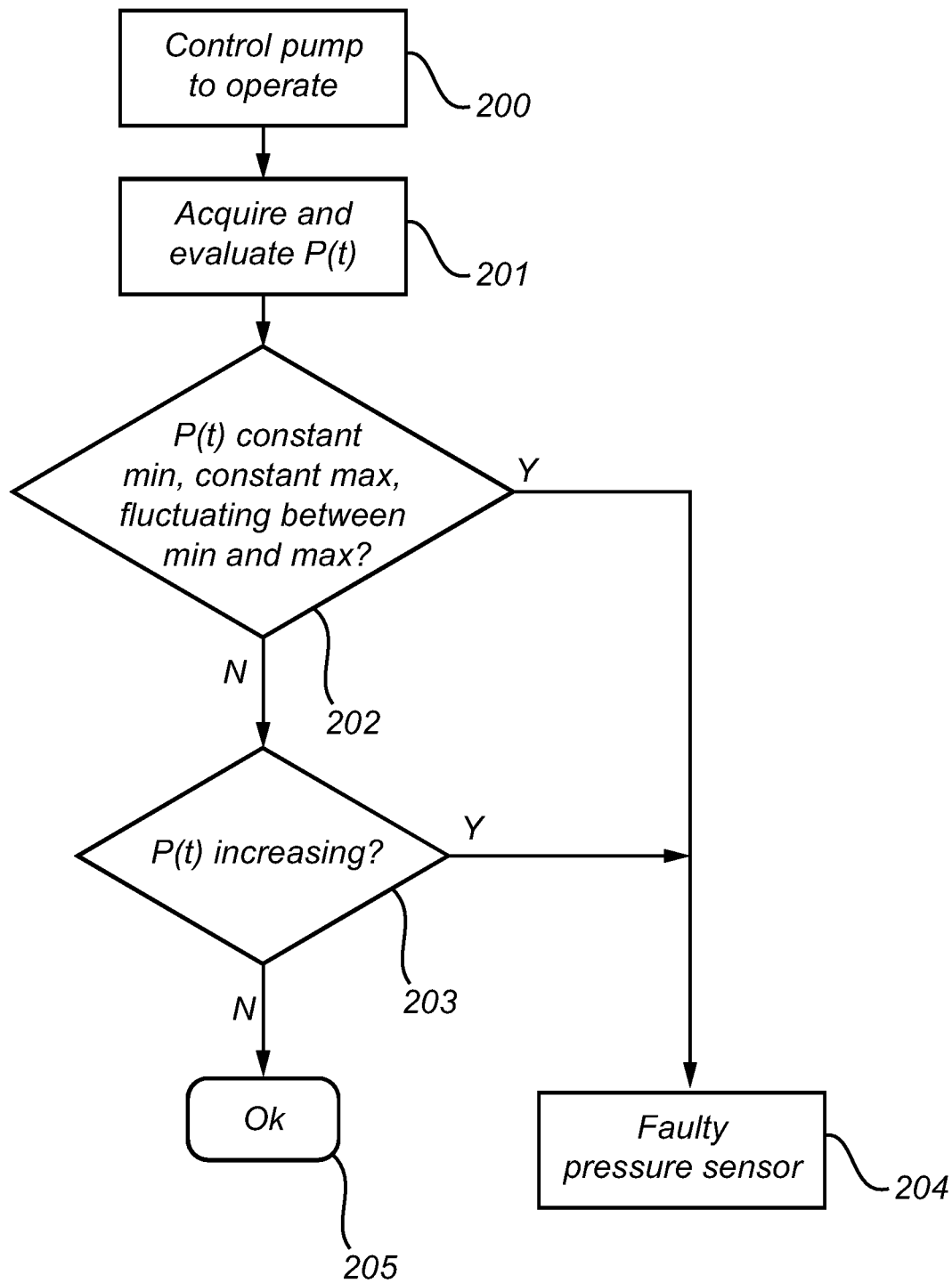
FIG. 3 is a flow-chart illustrating a second example configuration of the mobile NPWT device according to embodiments of the present invention.
Figure 4:
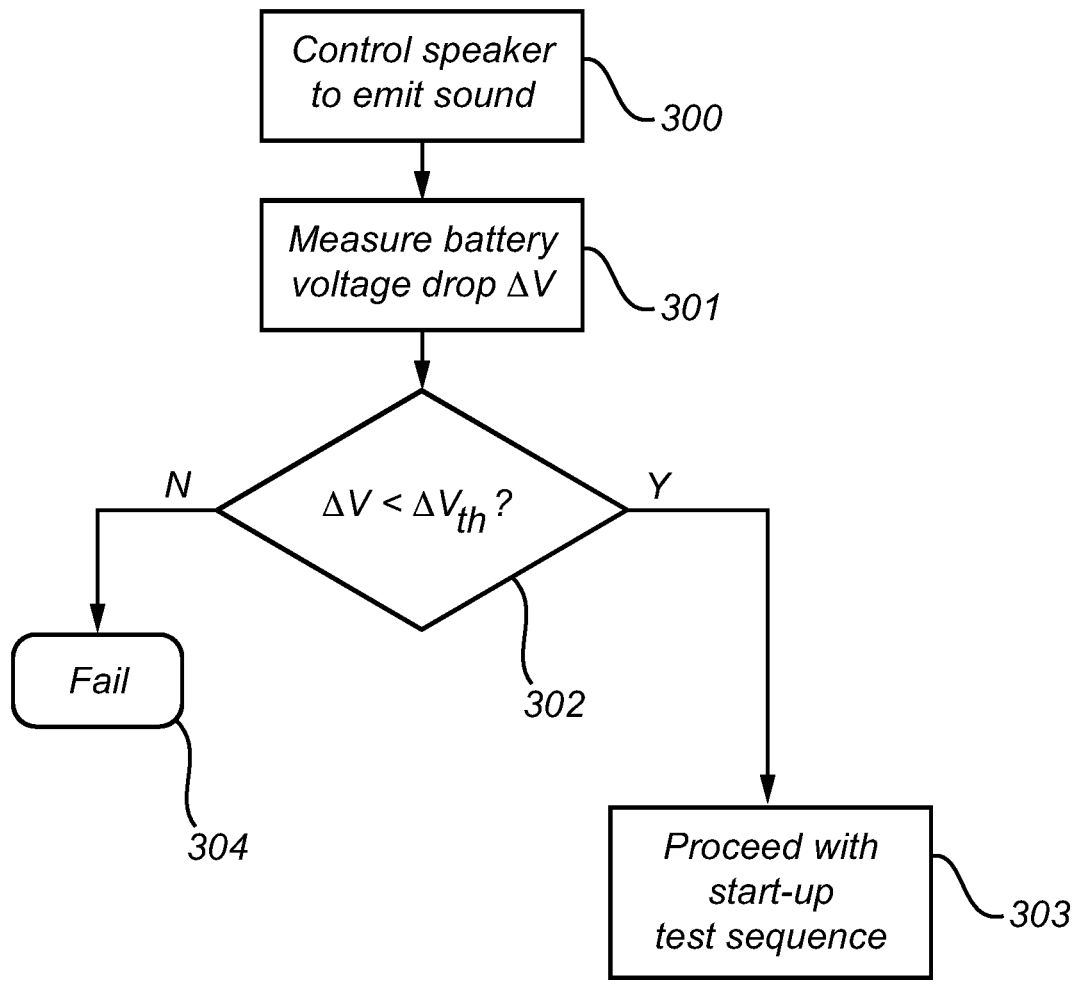
FIG. 4 is a flow-chart illustrating a third example configuration of the mobile NPWT device according to embodiments of the present invention.

In the following, embodiments of the present invention will be described with reference to the flow charts in FIG. 2, FIG. 3, and FIG. 4, in addition to the illustration in FIG. 1.

Figure 2:
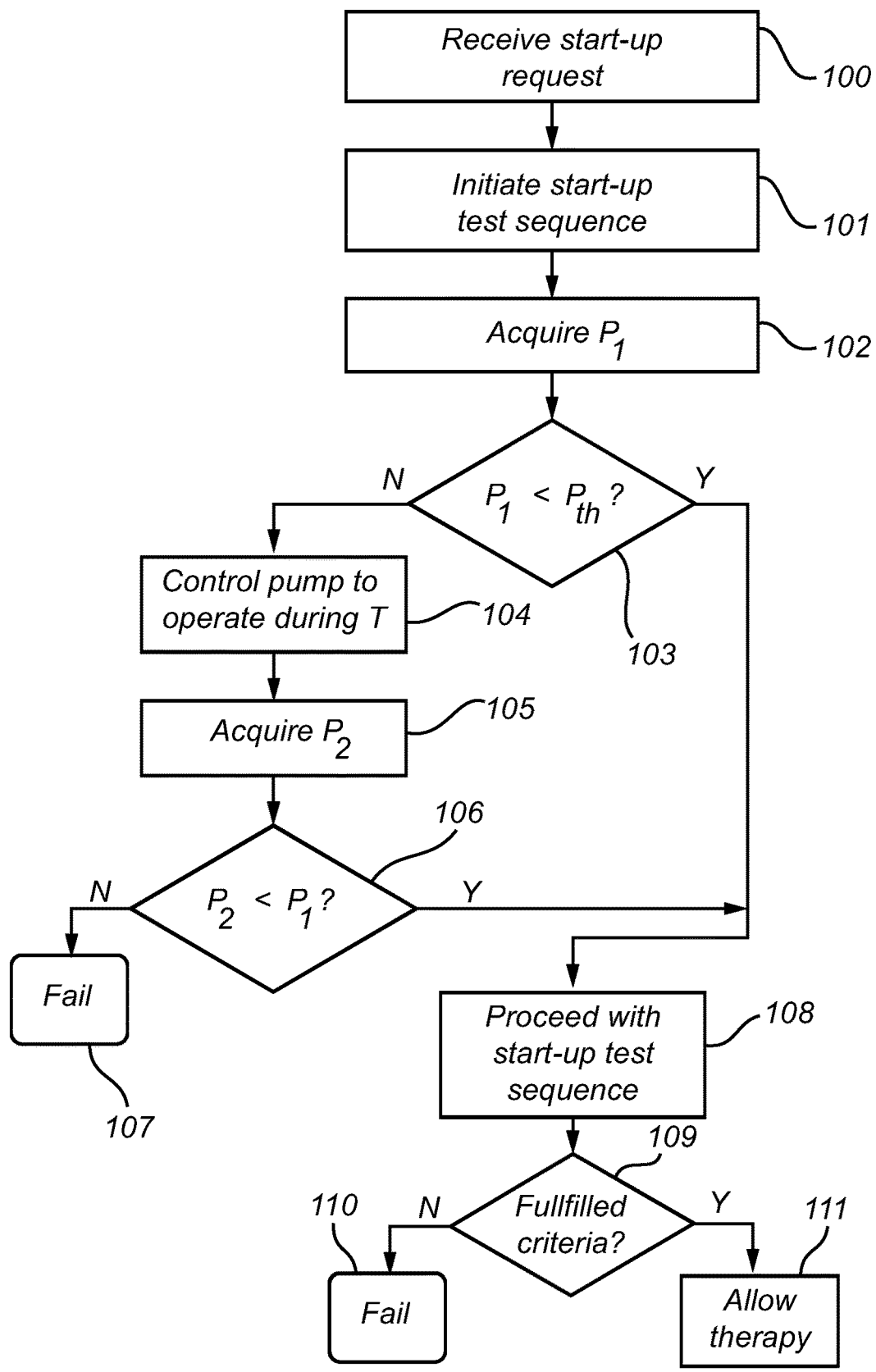
FIG. 2 is a flow-chart illustrating a first example configuration of the mobile NPWT device according to embodiments of the present invention.

FIG. 2 is a flow-chart illustrating a first example configuration of the mobile NPWT device according to embodiments of the present invention. Referring to FIG. 2, the control unit 21 of the NPWT device 3 may be configured to receive 100 a start-up request, which may for example be provided in the form of pre-defined operation of a button, or a reset switch, or power up following replacement of the battery pack 19.

In response to the request for start-up, the control unit 21 is configured to initiate 101 a start-up test sequence for the NPWT device 3.

As a part of the start-up test sequence, the control unit 21 is configured to acquire 102, from the pressure sensor 23 a first signal $P_1$ indicating the pressure in the canister 15.

The control unit 21 is configured to evaluate 103 the first signal $P_1$ acquired from the pressure sensor 23, and when the first signal $P_1$ indicates a pressure less negative than a predefined threshold pressure $P_{th}$, the control unit 21 is configured to control 104 the pump 13 to operate during a predefined time period T, and to acquire 105 a second signal $P_2$, indicating a pressure in the canister 15, after the predefined time period T.

The control unit 21 is configured to evaluate 106 the second signal $P_2$ acquired from the pressure sensor 23 after the predefined time period T, and when the second signal $P_2$ indicates that the pressure has not become more negative, or not sufficiently more negative to provide an indication that the pump 13 is operating as desired, the control unit 21 may be configured to determine 107 that the NPWT device 3 has failed the start-up test.

When, on the other hand, the second signal $P_2$ indicates that the pressure in the canister 15 has become more negative (or sufficiently more negative) than the pressure indicated by the first signal $P_1$, the control unit 21 is configured to proceed 108 with the start-up test sequence, and to determine 109 if the NPWT device 3 has failed 110 the start-up test, or passed the start-up test. If the start-up test is determined by the control unit 21 to have been passed by the NPWT device 3, the control unit 21 may be configured to allow 111 the NPWT device 3 to transition to therapy mode.

When the NPWT device 3 has been allowed to transition to therapy mode, the control unit 21 may be configured to directly transition the NPWT device 3 to therapy mode, or to do this in response to a user request, such as a predefined operation of a user interface, such as a button or a touch screen. The predefined time period T may advantageously be at least 500 ms in order to ensure that a reliable indication of whether or not the pump 13 and/or pressure sensor 23 is/are operational, regardless of the configuration of the NPWT system 1. Even more advantageously, the predefined time period may be at least 700 ms, such as 900 ms.

After the control unit 21 has allowed the NPWT device 3 to transition to the therapy mode, or as a part of the start-up test sequence, the control unit 21 may be configured to take additional steps to test operation of the pump 13 and/or the pressure sensor 23 of the NPWT device 3. Such a second example configuration of the mobile NPWT device according to embodiments of the present invention is schematically illustrated in FIG. 3. Referring to FIG. 3, the control unit 21 of the NPWT device 3 may thus additionally be configured to control 200 the pump 13 to operate, and to repeatedly acquire 201 signals P(t) from the pressure sensor 23 while the pump 13 is operating.

During or following acquisition of the signals P(t) from the pressure sensor 23, the control unit 21 may be configured to evaluate the signals P(t) from the pressure sensor 23 to determine if at least one of two failure modes can be identified. When it is determined 202 that the signals P(t) acquired from the pressure sensor 23 are constantly at a minimum value $P_{min}$ that can be acquired from the pressure sensor 23, or the signals P(t) acquired from the pressure sensor 23 are constantly at a maximum value $P_{max}$ that can be acquired from the pressure sensor 23, or the signals P(t) acquired from the pressure sensor 23 alternate between the minimum value $P_{min}$ and the maximum value $P_{max}$, the control unit 21 may be configured to identify a first failure mode indicating a broken connection between the control unit 21 and the pressure sensor 23. When it is determined 203 that the signals P(t) acquired from the pressure sensor 23 indicate a pressure that increases over time, the control unit 21 may be configured to identify a second failure mode indicating malfunctioning amplification circuitry in the pressure sensor 23.

When either of these failure modes is identified by the control unit 21, the control unit is configured to determine 204 that signals P(t) from the pressure sensor 23 are unreliable, and that the pressure sensor 23 should therefore be classified as faulty. In such a case, the control unit 21 may be configured to take action by preventing the NPWT 3 from entering the therapy mode or interrupting therapy. The control unit 21 may also be configured to provide an indication to the user via a user interface.

When none of these failure modes is identified by the control unit 21, the control unit is configured to determine 205 that the pressure sensor 23 works as intended, and may allow the NPWT 3 to enter or continue the therapy mode.

As a part of the start-up test sequence, the control unit 21 may be configured to take additional steps to test operation of the NPWT device 3. Such a third example configuration of the mobile NPWT device 3 according to embodiments of the present invention is schematically illustrated in FIG. 4. Referring to FIG. 4, the control unit 21 of the NPWT device 3 may thus additionally be configured to control 300 the speaker 24 to emit sound. Since the speaker 24 is one of the most power hungry components of the NPWT device 3, this may be an efficient way of evaluating the health of the battery pack 19. According to instructions, a depleted battery pack 19 should be replaced by a fully charged or new battery pack 19. If, however, instructions are not followed, a depleted battery pack 19 may be replaced by another at least partly depleted battery pack 19.

Accordingly, the control unit 21 may be configured to measure 301 a battery voltage drop $\Delta V$ resulting from the operation of the speaker 24.

The control unit 21 may be configured to evaluate 302 the measured battery voltage drop $\Delta V$ in relation to a predefined threshold voltage drop $\Delta V_{th}$, and to determine 303, when the drop in battery voltage during operation of the speaker is less than the predefined threshold voltage drop $\Delta V_{th}$, that the NPWT device has fulfilled a criterion in the set of predefined criteria, so that the start-up test sequence can proceed.

When the control unit 21 instead determines that the measured battery voltage drop $\Delta V$ is greater than the predefined threshold voltage drop $\Delta V_{th}$, the control unit 21 may be configured to determine 304 that the NPWT device 3 has failed the start-up test.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A mobile negative pressure wound therapy (NPWT) device, comprising:
   an inlet configured to be in fluid flow connection with a wound site;
   a canister in fluid flow connection with the inlet for collection of liquid from the wound site;
   a pump in fluid flow connection with the canister for establishing a negative pressure in the canister;
   a pressure sensor arranged to sense a pressure in the canister; and
   control circuitry for controlling operation of the NPWT device, the control circuitry being configured to:
   receive a request for start-up of the NPWT device;
   initiate, in response to the request for start-up, a start-up test sequence for the NPWT device;
   acquire, from the pressure sensor, a first signal indicating the pressure in the canister;
   evaluate the first signal acquired from the pressure sensor;
   when the acquired first signal indicates a pressure less negative than a predefined threshold pressure:
      control the pump to operate during a predefined time period;
      acquire a second signal from the pressure sensor after the predefined time period;
      proceed with the start-up test sequence; and
      allow, unless the NPWT device failed at least one test in the start-up test sequence by failing to fulfill at least one criterion in a set of predefined criteria, the NPWT device to transition to therapy mode; and
   when the acquired first signal indicates a pressure more negative than the predefined threshold pressure:
      proceed with the start-up test sequence without controlling the pump to operate during the predefined time period; and
      allow, unless the NPWT device failed at least one test in the start-up test sequence by failing to fulfill at least one criterion in a set of predefined criteria, the NPWT device to transition to therapy mode.

2. The NPWT device according to claim 1, wherein, when the acquired first signal indicates a pressure less negative than the predefined threshold pressure, the control unit is further configured to:
   evaluate the second signal acquired from the pressure sensor; and
   determine, when the second signal indicates a negative pressure within a predefined interval, that the NPWT device has fulfilled a criterion in the set of predefined criteria.

3. The NPWT device according to claim 1, wherein, when the acquired first signal indicates a pressure more negative than the predefined threshold pressure, the control unit is further configured to:
   determine that the NPWT has fulfilled a criterion in the set of predefined criteria, without controlling the pump to operate during the predefined time period.

4. The NPWT device according to claim 1, wherein the control unit is further configured to, after the NPWT device has been allowed to transition to therapy mode:
   repeatedly acquire signals from the pressure sensor;
   evaluate the signals acquired from the pressure sensor; and
   determine that the pressure sensor is non-functional when:
   the signals acquired from the pressure sensor are constantly at a minimum value that can be acquired from the pressure sensor, or the signals acquired from the pressure sensor are constantly at a maximum value that can be acquired from the pressure sensor, or the signals acquired from the pressure sensor alternate between the minimum value and the maximum value; or
   the signals acquired from the pressure sensor indicate a pressure that is constant or increases over time while the pump is operating.

5. The NPWT device according to claim 1, wherein the NPWT device further comprises a battery and a speaker, and the control circuitry is further configured to:
   control the speaker to operate to emit a sound;
   measure a drop in battery voltage during operation of the speaker; and
   determine, when the drop in battery voltage during operation of the speaker is less than a predetermined value, that the NPWT device has fulfilled a criterion in the set of predefined criteria.

6. A method of testing a mobile negative pressure wound therapy (NPWT) device having an inlet configured to be in fluid flow connection with a wound site, a canister in fluid flow connection with the inlet for collection of liquid from the wound site, a pump in fluid flow connection with the canister for establishing a negative pressure in the canister, and a pressure sensor arranged to sense a pressure in the canister, the method comprising the steps of:
   receiving a request for start-up of the NPWT device;
   initiating, in response to the request for start-up, a start-up test including a start-up test sequence for the NPWT device;
   acquiring, from the pressure sensor, a first signal indicating the pressure in the canister;
   evaluating the first signal acquired from the pressure sensor;
   when the acquired first signal indicates a pressure less negative than a predefined threshold pressure:
      controlling the pump to operate during a predefined time period;

acquiring a second signal from the pressure sensor after the predefined time period;

proceeding with the start-up test sequence; and determining, unless the NPWT device failed at least one test in the start-up test sequence by failing to fulfill at least one criterion in a set of predefined criteria, that the NPWT device passed the start-up test; and when the acquired first signal indicates a pressure more negative than the predefined threshold pressure:

proceeding with the start-up test sequence without controlling the pump to operate during the predefined time period; and determining, unless the NPWT device failed at least one test in the start-up test sequence by failing to fulfill at least one criterion in a set of predefined criteria, that the NPWT device passed the start-up test.

7. The method according to claim 6, wherein the method further comprises the steps of:

evaluating the second signal acquired from the pressure sensor; and determining, when the second signal indicates a negative pressure within a predefined interval, that the NPWT device has fulfilled a criterion in the set of predefined criteria.

8. The method according to claim 6, wherein, when the acquired first signal indicates a pressure more negative than the predefined threshold pressure, the method further comprises the step of:

determining that the NPWT has fulfilled a criterion in the set of predefined criteria, without controlling the pump to operate during the predefined time period.

9. The method according to claim 6, wherein the method further comprises the following steps, performed after it has been determined that the NPWT device passed the start-up test:

repeatedly acquiring signals from the pressure sensor;

evaluating the signals acquired from the pressure sensor; and determining that the pressure sensor is non-functional when:

the signals acquired from the pressure sensor are constantly at a minimum value that can be acquired from the pressure sensor, or the signals acquired from the pressure sensor are constantly at a maximum value that can be acquired from the pressure sensor, or the signals acquired from the pressure sensor alternate between the minimum value and the maximum value; or the signals acquired from the pressure sensor indicate a pressure that is constant or increases over time while the pump is operating.

10. The method according to claim 6, wherein the mobile NPWT device further comprises a battery and a speaker, and the start-up test sequence further comprises the following steps:

controlling the speaker to operate to emit a sound;

measuring a drop in battery voltage during operation of the speaker; and determining, when the drop in battery voltage during operation of the speaker is less than a predetermined value, that the NPWT device has fulfilled a criterion in the set of predefined criteria.

11. A non-transitory computer readable medium comprising instructions for causing a control unit comprised in a NPWT device to carry out the steps of a method comprising:

receiving a request for start-up of the NPWT device;

initiating, in response to the request for start-up, a start-up test including a start-up test sequence for the NPWT device;

acquiring, from a pressure sensor of the NPWT device, a first signal indicating the pressure in a canister of the NPWT device;

evaluating the first signal acquired from the pressure sensor;

when the acquired first signal indicates a pressure less negative than a predefined threshold pressure:

controlling a pump of the NPWT device to operate during a predefined time period;

acquiring a second signal from the pressure sensor after the predefined time period;

proceeding with the start-up test sequence; and determining, unless the NPWT device failed at least one test in the start-up test sequence by failing to fulfill at least one criterion in a set of predefined criteria, that the NPWT device passed the start-up test; and when the acquired first signal indicates a pressure more negative than the predefined threshold pressure:

proceeding with the start-up test sequence without controlling the pump to operate during the predefined time period; and determining, unless the NPWT device failed at least one test in the start-up test sequence by failing to fulfill at least one criterion in a set of predefined criteria, that the NPWT device passed the start-up test, wherein the computer program is run on the control unit.

12. A negative pressure wound therapy (NPWT) system, comprising:

a chamber for establishment of a negative pressure, to be arranged at a wound site, the chamber having an outlet;

the NPWT device according to claim 1; and tubing flow connecting the outlet of the chamber and the inlet of the NPWT device.

13. The NPWT system according to claim 12, wherein the chamber further has an inlet in flow connection with an ambient through a filter, to provide for continuous leakage of air into the chamber.

* * * * *